United States Patent [19]
Quinn et al.

[11] Patent Number: 5,895,218
[45] Date of Patent: Apr. 20, 1999

[54] DENTAL TRAY

[75] Inventors: Michael J. Quinn, Wildwood; D. Keith Chipman, Ste. Genevieve, both of Mo.

[73] Assignee: Young Dental Manufacturing Company, Earth City, Mo.

[21] Appl. No.: 09/131,476

[22] Filed: Aug. 10, 1998

[51] Int. Cl.⁶ ................................................ A61C 17/02
[52] U.S. Cl. .......................... 433/80; 433/42; 433/215; 128/862
[58] Field of Search .......................... 433/80, 215, 6, 433/37, 41, 42, 43, 47, 46, 45, 48, 71; 128/848, 857, 859, 862; 602/902

[56] References Cited

U.S. PATENT DOCUMENTS

| | | | |
|---|---|---|---|
| 900,541 | 10/1908 | Holmes | 433/43 |
| 4,173,219 | 11/1979 | Lentine | 128/848 |
| 4,376,628 | 3/1983 | Aardse | 433/42 |
| 4,544,354 | 10/1985 | Gores et al. | 433/42 |
| 5,297,960 | 3/1994 | Burns | 433/42 |
| 5,336,086 | 8/1994 | Simmen et al. | 433/37 |
| 5,460,527 | 10/1995 | Kittelsen | 433/215 |
| 5,642,737 | 7/1997 | Parks | 128/848 |
| 5,823,193 | 10/1998 | Singer et al. | 128/848 |

Primary Examiner—Gene Mancene
Assistant Examiner—Pedro Philogene
Attorney, Agent, or Firm—Polster, Lieder, Woodruff & Lucchesi

[57] ABSTRACT

A dental tray of the present invention includes a body made from a generally fluid impervious material (preferably a closed cell foam) having a bottom and side walls to define an arched channel sized and shaped to fit over a patient's teeth. A deformable, arched gasket is fixed to the body along an upper edge of the body wall. The gasket extends inwardly from the tray body wall and defines an arched slot. The gasket inner edge contacts and seals against the patient's gums and teeth when the tray is applied to the patient's teeth to substantially prevent compounds from leaking from the sides or back of the tray during use of the tray. Preferably, two identical trays are connected together by a connector. The connector is adhered to the base of the trays, generally at a front of the trays. The connector is folded over upon itself when the two trays are inserted in a patient's mouth and define a handle. The handle extends through the patient's lips from a position generally between the patient's teeth. The trays may be pre-filled with the compound or medicament to be applied to the patient's teeth. If so, the tray is sealed to prevent loss of the compound or medicament during transportation and storage of the trays. The trays are also individually wrapped.

35 Claims, 6 Drawing Sheets

DENTAL TRAY

CROSS-REFERENCE TO RELATED APPLICATIONS

Not applicable

STATEMENT REGARDING FEDERALLY SPONSORED RESEARCH OR DEVELOPMENT

Not Applicable.

BACKGROUND OF THE INVENTION

This invention relates to dental trays for applying a dental compound, such as a fluoride, whitener, etc. to a patient's teeth during a dental procedure, and in particular to a disposable tray which seals against the patient's teeth and/or gums.

Dental trays have long been used to apply compounds, such as fluoride, to patients' teeth. Typically, the trays comprise a pair of arched channels which hold the compound. The trays are sized and shaped to be inserted in a patient's mouth over the patient's teeth. Early trays were rigid, and were commonly made of metal. These trays did not allow for expansion or contraction of the trays to compensate for the different sized arches of patient's mouths. Thus, several trays had to be available so that a proper sized tray could be used on a patient. This could necessitate the use of several trays in a patient's mouth before the appropriate sized tray was found. This would obviously contaminate several trays, only one of which would ultimately be used, and all of which would require cleaning before they could be used again. Thus, not only did the use of rigid trays require extra cleaning, but because they were rigid, they were generally uncomfortable for the patient.

When the trays were made of metal, the trays for the upper and lower teeth were separate from each other. When trays were begun to be made of moldable materials, such as plastics and foams, the trays' upper and lower portions were connected together by a connector or hinge. On some models, the hinge was in the back of the trays. This increased the overall length of the assembly, and for patients with small mouths, made the trays uncomfortable to use. Typically, the hinge element which attaches the upper and lower trays in the back of the trays contacts the back of the patient's jaw at the temporomandibular joint. This is a sensitive spot in a patient's mouth, and the contact of the tray with the jaw at this point often activates the gag reflex, making such trays unsuitable for use, especially on people with smaller mouths.

On other trays, the hinge was formed in the front of the tray assembly, and defined a tab or handle when the tray is inserted in a patient's mouth. Such a handle facilitated insertion of the tray into the patient's mouth and removal of the tray from the patient's mouth. However, the handles for such trays are typically located at the tops of the trays (i.e., the openings of the trays), making them uncomfortable for the patient. Such a tray is shown for example in U.S. Pat. No. 4,173,219 to Lentine. This position of the handle interferes with the patient's lips. In order for the handle to protrude from between the patient's lips, when the mouth is closed, the handle must be bent at two locations, to form an L-shaped element. However, due to the natural resiliency of the material from which the handles are made, the handles will inevitably urge the patient's lips apart. As can be appreciated, this will not be a very natural position for the patient, and the patient may not be comfortable while the tray is in use.

Another problem with the prior trays is that they do not seal well against the patient's teeth or gums. Typically, there are openings through which the compound can escape the tray. This leakage of the compound has long been a problem because the compound which leaks out of the tray is not applied to the teeth and, therefore is wasted. Further, leakage of the compound from the tray into the patient's mouth can cause the patient to gag. Additionally, the compound often does not have a pleasing taste. Various designs have attempted to create a seal. For example, the above noted U.S. Pat. No. 4,173,219 provides for a flange which extends outwardly from the rim of the tray. A similar tray is shown in U.S. Pat. No. 5,211,559 to Hart. However, when the trays shown in these patents are expanded, for example to fit the arch of a larger mouth, the flange on the lingual side of the tray will cause the distance between the lingual and buccal walls of the trays to pull apart. This will make the depth of the tray to become more shallow, and create gaps through which the compound can escape.

Additionally, dental trays are typically packaged in bundles. That is, a plurality (i.e., 20, 50, 100, etc.) are packaged together inside of a single bag or other packaging. This common packaging can lead to cross-contamination. When a dental practitioner (dentist, hygienist, technician, etc.) reaches into the bag to grab one tray, the practitioner will come into contact with other trays as well. Unless the practitioner has a tray ready prior to the dental examination, or unless he removes the gloves he is currently wearing and dons a new pair of gloves to retrieve the dental tray, the other trays in the package will become contaminated.

BRIEF SUMMARY OF THE INVENTION

Briefly stated, a dental tray of the present invention is provided to apply a compound or medicament to a patient's teeth. Importantly, the tray is formed such that it will substantially prevent the compound in the tray from leaking from the tray when the tray is applied to the patient's teeth. The tray includes a deformable body made from a generally fluid impervious material (preferably a closed cell foam). The body has a bottom and side walls to define an arched channel sized and shaped to fit over a patient's teeth and a flange extending inwardly from a top of the tray wall. The flange defines a slot through which the patient's teeth extend to be received in the tray channel. The flange is sized and shaped to seal with the lingual and buccal surfaces of the patient's gums and with a back surface of the patient's back teeth. Preferably, the flange is made from a deformable gasket (preferably made from an open-celled foam) which is fixed to the body along an upper edge of the body wall. The gasket slot is narrower than the width of the patient's teeth. Preferably, the slot has a width ranging from between about 0.05" to about 0.25". The change in the slot width accommodates the changing width in a person's teeth, from the front teeth, which are narrow to the back molars which are wider. The gasket has buccal and lingual portions joined by a curved back portion. The buccal and lingual portions are of generally the same width. The back portion, however, is wider than the buccal and lingual portions. This increased portion enhances the seal between the gasket and the patient's mouth.

To better fit the patient's teeth, the depth of the dental tray channel tapers from front to back, such that the back of the channel is shallower than the front of the channel. The taper is from about 2° to about 17°, and preferably about 5°.

The dental tray is provided with a handle which extends from the bottom of the tray, at the front of the tray.

Preferably, two trays are connected together by a connector, which is folded over to form the handle. Because the handle extends from the base or bottom of the trays, it will extend from between the patient's teeth and lips without the need to be bent.

The trays can be sold empty or pre-filled with the compound or medicament to be applied to the teeth. If the tray is to be pre-filled, the channel of the tray is sealed to prevent the compound or medicament in the tray from flowing out of the tray prior to use of the tray. The tray can be sealed by applying a shrink wrap around the whole tray; by placing a cover over the tray to close the channel; or by providing a sheet having a line of weakness corresponding to the shape of the slot. When the portion of the sheet defined by the line of weakness is removed, the sheet will form the flanges which extend over the channel and the slot which allows for access to the channel.

Whether or not the tray is provided empty to be filled by the practitioner, or pre-filled, the trays are preferably individually wrapped, so that an individual tray can be removed from a box containing a plurality of trays without contaminating any of the remaining trays in the box.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention.

Figure 4:
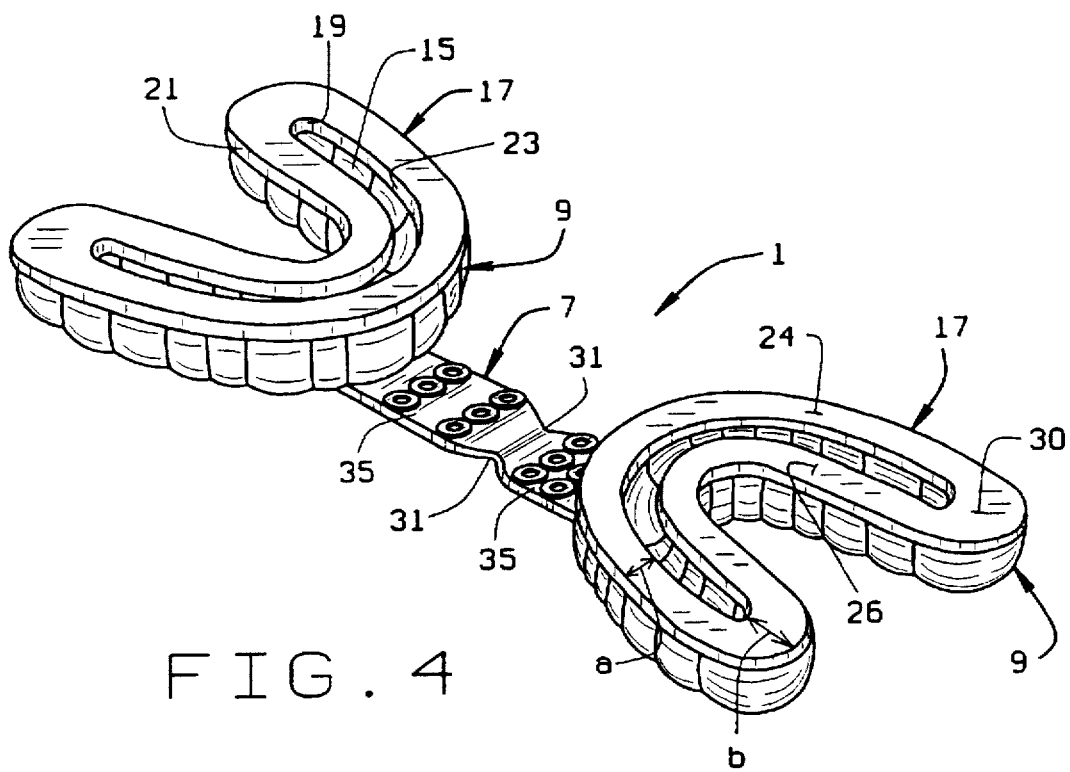
FIG. 4 is a top perspective view of the tray assembly in the unfolded state.

A dental tray assembly 1 of the present invention includes an upper tray 3 and a lower tray 5 which are connected by a connector 7. The connector 7 is formed to be bent or folded about its middle to bring the upper and lower trays from the position shown FIG. 4 in which the trays can be filled with a compound, to the position shown in FIG. 1 wherein the bottoms or bases of the trays are adjacent each other so that the tray assembly can be inserted in a patient's mouth. The connector can be a foam connector which, due to its properties is easily folded over upon itself. Alternately, the connector can be a more rigid plastic strip which is hinged (i.e., is provided with a living hinge, for example). The use of a more rigid plastic connector would provide more rigidity to the assembly than the foam connector. That is, it would be more difficult to slide the upper and lower trays laterally relative to each other, so that they will stay more in line with each other.

Figure 8:
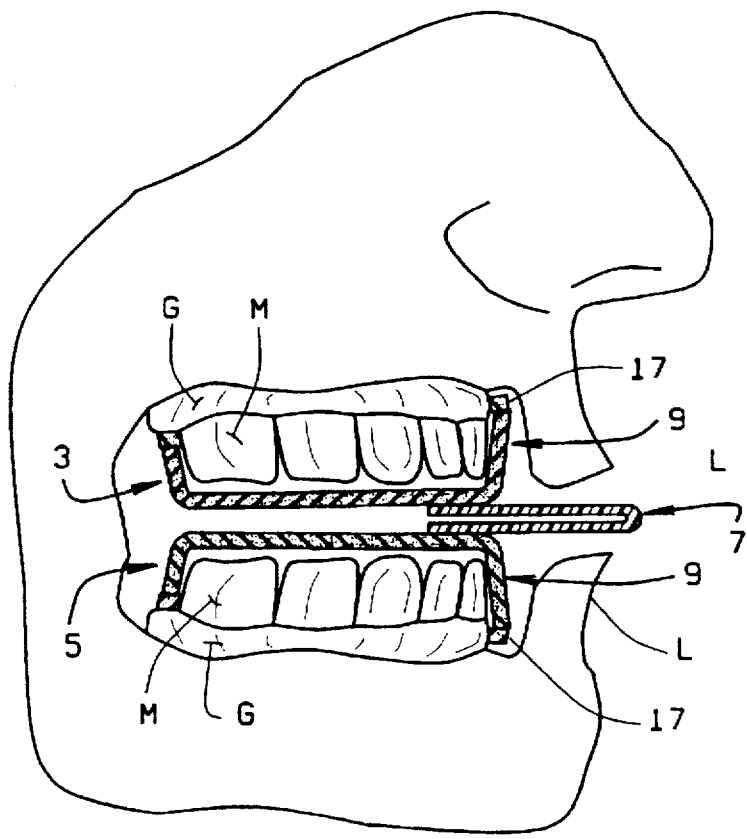
FIG. 8 is a view showing the tray assembly positioned in a patient's mouth, with the handle of the tray assembly extending from between the patient's lips without unduly distorting the patient's lips.

The trays 3 and 5, which are identical, include a unitary, one-piece body 9 and a gasket 17. Rather than being identical, the trays 3 and 5 could be shaped differently from each other so that they will correspond more accurately to the shape of the upper and lower arches of the mouth. The body 9 is preferably flexible and is preferably made of a closed-cell foam. The body 9 has a base or bottom 11 and side walls 13 which define an opened generally U-shaped or arched channel 15. The channel is shaped to correspond generally to the curvature of the teeth in a patient's mouth, so that the tray can be applied to the teeth. The channel 15 is sufficiently deep such that when the tray is applied to the patient's mouth, the gasket 17 will bear against the patient's gums above the gum line and the teeth will be fully enclosed in the channel 15, as seen in FIG. 8. To facilitate the fit of the tray to the teeth, the depth of the tray varies from the front (where the teeth extend above the gum line the most) to the back (where the teeth are shortest and extend above gum line the least). Preferably, the change in depth of the channel is linear, and the channel has about a 5° taper. However, this taper in the depth of the tray can vary for different sized trays, and can be as little as 2° and as much as 17°. This taper to the tray depth enables the tray to follow the upper surfaces of typical teeth. It therefore minimizes the amount of space between the teeth and the base of the trays. If the trays were of a uniform depth, there would be a significant amount of space between the rear molars and the base of the tray. This would thus require that more compound be used to fill the tray, and would make the tray less comfortable for the patient.

As noted, the tray is preferably made of a foam. This allows for the tray to be generally flexible. The ends of the tray can thus be pulled apart or brought together so that a single tray can fit a range of arch widths. A single tray therefore can be used to fit a large range of mouths sizes.

The tray body 9 is preferably formed by vacuum thermoforming. To make the body 9, it is first formed in a mold, and once formed, the tray is cut from the mold such that there is no web or flange extending out from the walls of the tray, as there is with the trays noted in U.S. Pat. Nos. 4,173,219 and 5,211,559. The formation of such flanges on the walls of the tray interfere with ability of the tray to be expanded, as noted above. By eliminating the webs of the prior trays, the distance between the buccal and lingual walls of the tray will remain substantially constant, even as the tray is expanded or contracted to fit wider or narrower mouth arches. Hence the ability of the tray to seal with the teeth or gums of the patient will not be affected by a widening or narrowing of the tray.

The gasket 17 is a one-piece gasket which is applied to the top of the body 9 and extends around the full circumference of the body at the top of the body. The gasket is a flexible gasket which can easily conform to the contours of the mouth to which it is applied. Preferably, the gasket 17 is a foam gasket made of an open-celled foam. The gasket 17 is fixed to the body 9 such as by RF welding. A weld W extends the full length of the tray wall. This weld will create a seal to prevent the compound from leaking out of the tray from between the gasket and the top of the tray walls. The gasket can be fixed to the body walls by any other appropriate means, such as by gluing, or using double-sided tape, for example.

The gasket 17 is generally arched, corresponding to the arch of the tray and generally to the arch of a patient's teeth. It has an outer edge 21 that is generally flush with the outer surfaces of the tray walls and an inner edge 23. The gasket inner edge 23 is spaced from the channel wall. The gasket inner edge 23 defines an arched slot 19 which permits access to the channel 15, so that a compound can be placed in the tray for application to a patient's teeth.

The slot 19 is narrower than the patient's teeth at all points. Thus, the slot 19 will have to be expanded to be applied over the teeth. Preferably, the slot varies in width, the slot being narrower in front (i.e., at the apex or center of the arch defined by the tray) and wider in back. Preferably, the slot varies from a width of about 0.05" at the front to a width of between 0.25" and 0.3" at the back. This variation in width will reduce the possibility of a gap forming between any one tooth and the gasket. This will ensure that the gasket engages the teeth and/or gums, to form a seal with the teeth and/or gums. Because the gasket is made of foam, it is flexible. The flexibility of the gasket will enhance its ability to seal against the teeth and/or gums, and to conform to the surfaces of the teeth and/or gums. Thus, there will be substantially no gaps between the teeth and/or gums and the gasket through which the compound in the tray can escape the tray. Thus, substantially all of the compound deposited in the channel 15 will be applied to the teeth.

Figure 7:
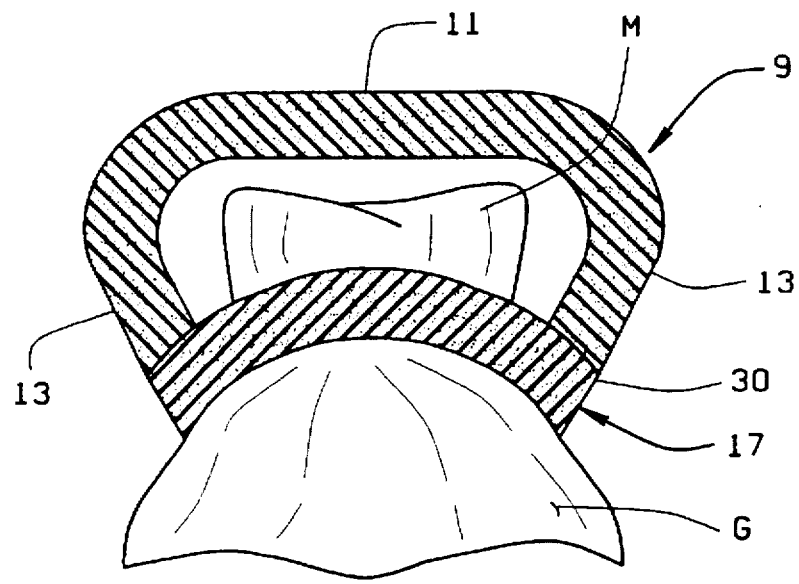
FIG. 7 is a cross-sectional view showing the manner in which the tray assembly seals with the patient's gums behind the back teeth.

The gasket 17 can be considered to have a buccal portion 24 and a lingual portion 26 which are connected by a back portion 30. (FIG. 4) The buccal and lingual portions generally are of the same width "a". The back portion 30, however, has a width "b" which is greater than the width "a" of the buccal and lingual portions. This variance in the width of the gasket facilitates the sealing of the gasket behind the back teeth of the mouth. As seen in FIG. 7, when the tray is applied to the teeth, the back portion 30 of the gasket will deform to correspond to the shape of the patient's gum behind the rear most molar M. This will tend to pull the side walls 13 of the tray inwardly toward each other. This inward flexion of the tray and the bending of the gasket back portion 30 will help the gasket to form a tighter seal against the patient's teeth and/or gums.

Figure 3:
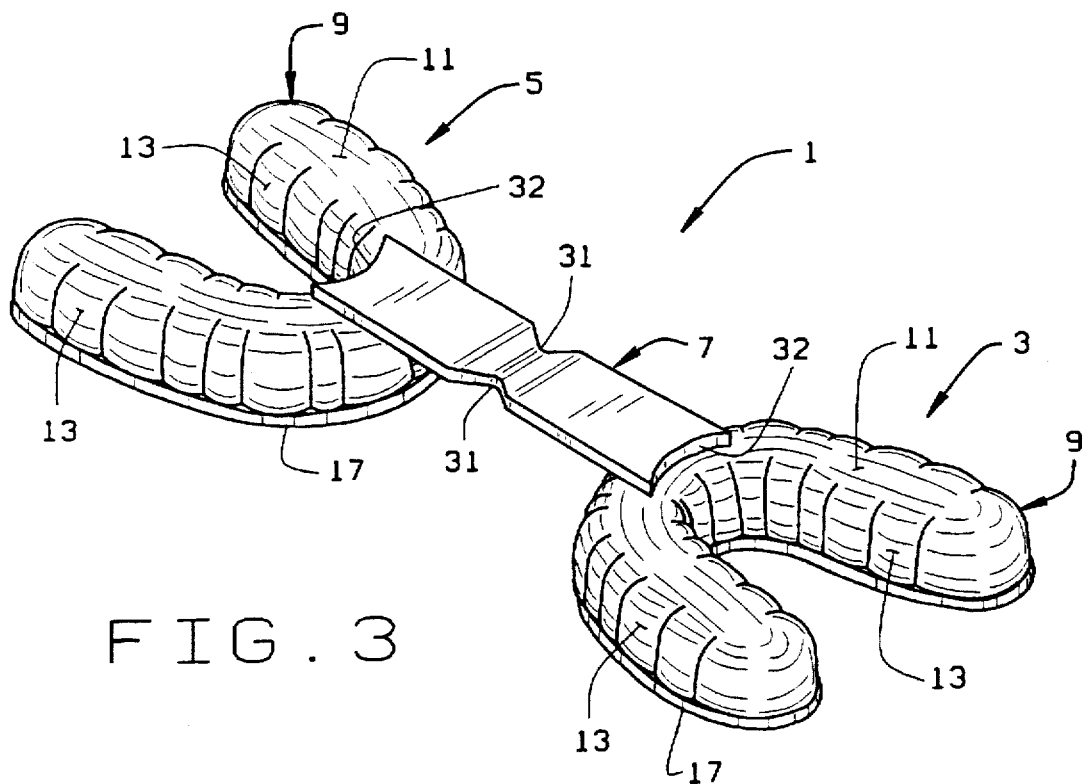
FIG. 3 is a bottom perspective view of the tray assembly in an unfolded state.

The connector 7 is fixed to the body 9 of the upper and lower trays 3 and 5 along the bottom or base 11 of the trays and at the front of the trays, as seen in FIG. 3, so that the connector will extend generally from the center or apex of the arch defined by the trays, when the trays are folded over, as seen in FIG. 8. This location of the connector 7 will enable the connector 7 to extend between the patient's lips L without any bending of the connector or any distortion of the patient's lips. This will make the tray more comfortable to the patient.

Figure 5:
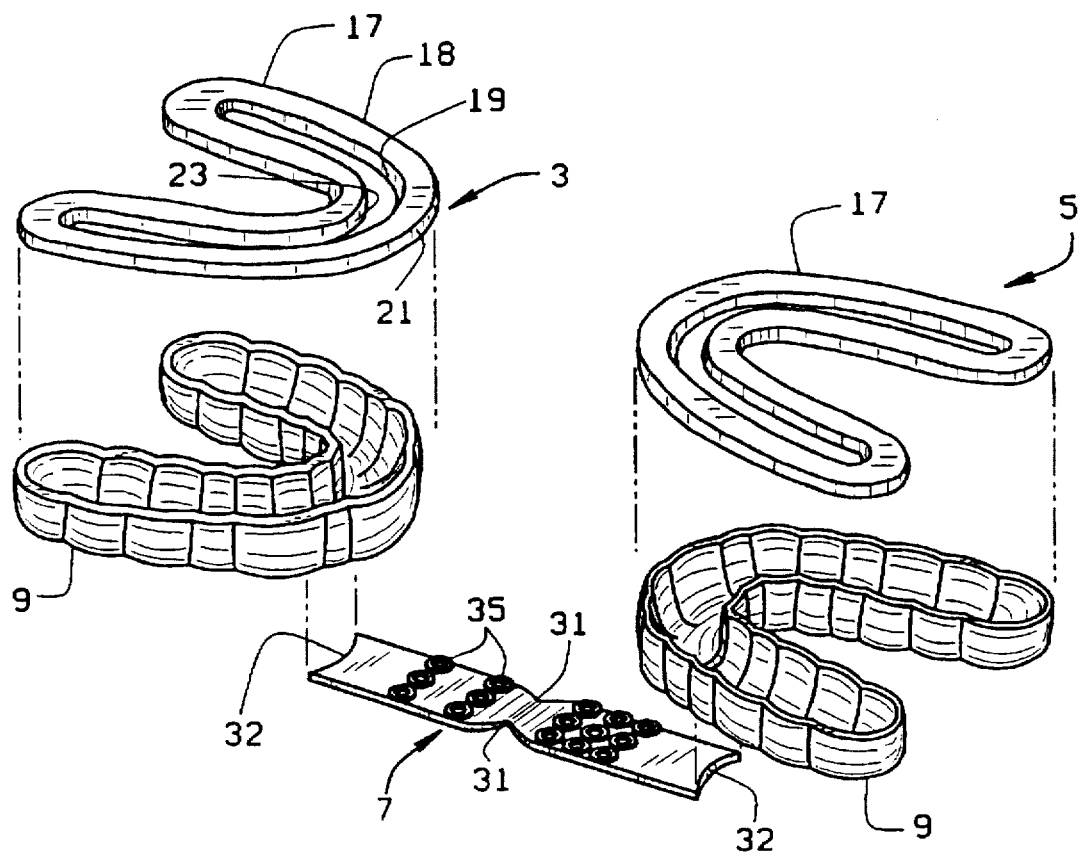
FIG. 5 is an exploded perspective view of the tray assembly.

The connector 7 is preferably formed as a separate piece and is fixed to the trays 3 and 5 by gluing, welding, or any other conventional means. The connector 7 has concavely curved ends 32 (FIGS. 3 and 5) which generally match the curvature of the inner or lingual wall of the trays. This substantially prevents any portion of the connector from extending beyond the lingual tray wall and inwardly into the patient's mouth, where it can be an irritant to the patient. This helps makes the tray more comfortable to the patient.

The connector 7 can alternatively be secured to the buccal wall of the tray. The connector 7 would then extend down at least a portion of the tray's buccal wall and then extend from the bottom of the wall. The connector would be fixed to the tray for the full distance it overlaps the buccal wall of the tray. In this embodiment, the connector 7 would effectively have an L-shape.

Figure 1:
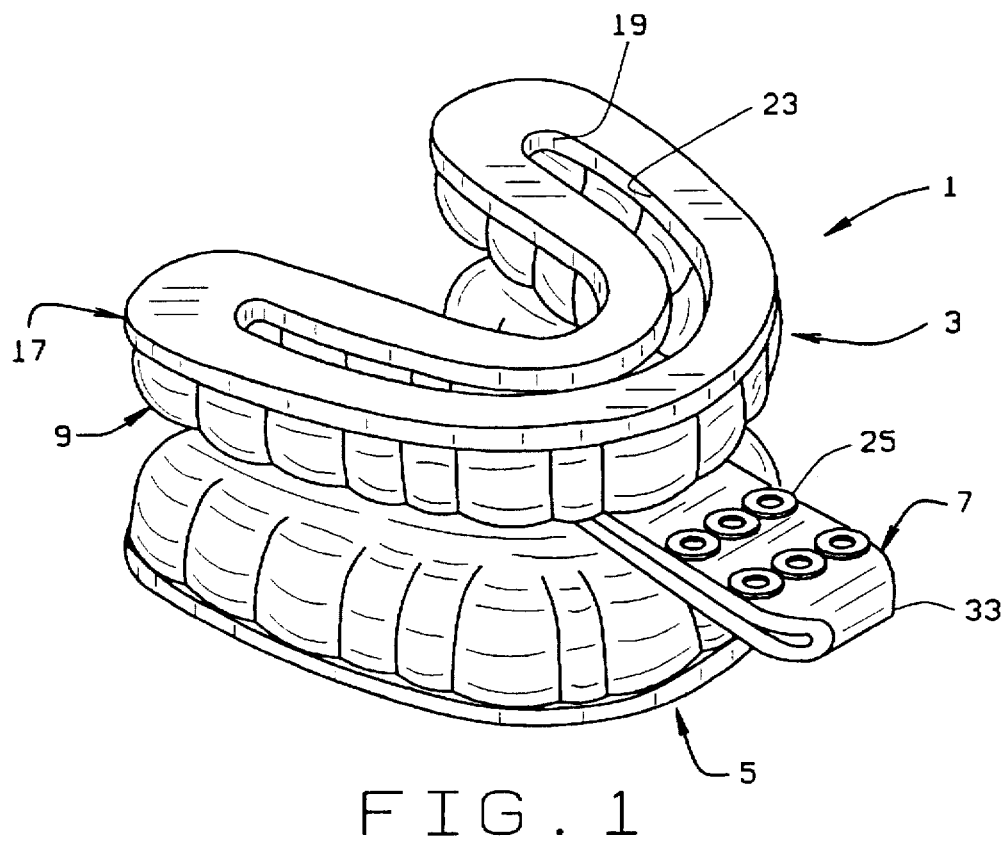
FIG. 1 is a perspective view of a dental tray assembly of the present invention having an upper tray and a lower tray which are connected together; the tray assembly being shown in a folded position for insertion into a patient's mouth.
Figure 2:
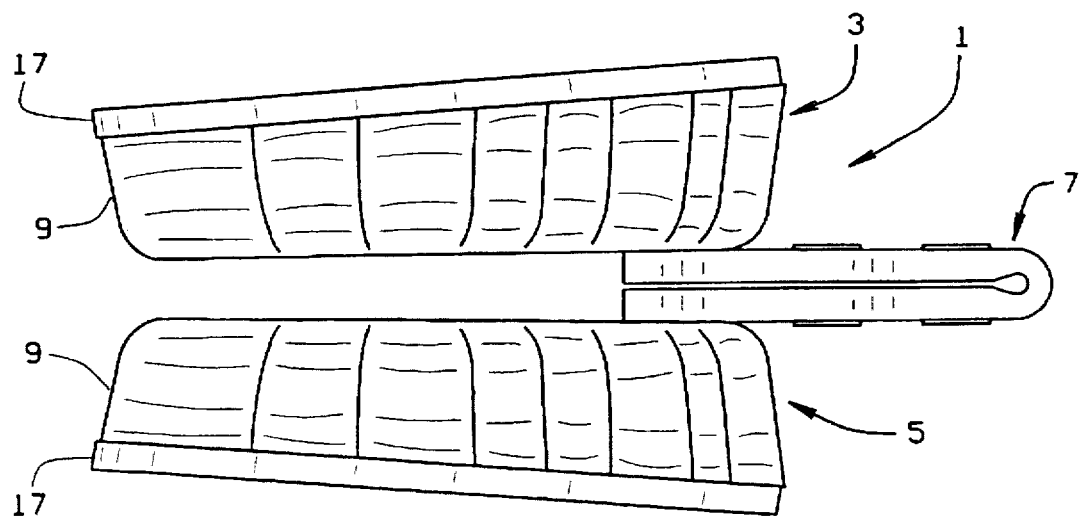
FIG. 2 is a side elevational view of the tray assembly in a folded position.

As seen in FIGS. 1 and 2, when the assembly 1 is folded over for insertion into a patient's mouth, the connector 7 folds over upon itself to define a handle which may easily be grasped by the practitioner. Because the connector extends from the bottoms 11 of the trays, the handle will extend from between the patient's teeth, and through the patient's lips without the need to be bent, as seen in FIG. 8. This position of the handle will allow the handle to protrude through the patient's lips, without causing the lips to be distorted. The handle, therefore, is more comfortable for the patient. The connector 7 can be relieved, as at 31, at the approximate midpoint of the connector to facilitate folding of the connector. This also gives the handle a somewhat rounded end 33. (FIG. 1) The connector 7 has one surface which, in part, is textured or provided with a raised pattern 35 to provide for a gripping surface for the practitioner.

The tray assembly 1 is provided in an assembled state, as seen in FIGS. 1–4. The tray assemblies are also preferably individually wrapped. Thus, although there can be several tray assemblies in a single box or package, the fact that they are individually wrapped will help prevent the contamination of other trays when an individual tray assembly is removed from the box of trays for use.

Figure 9:
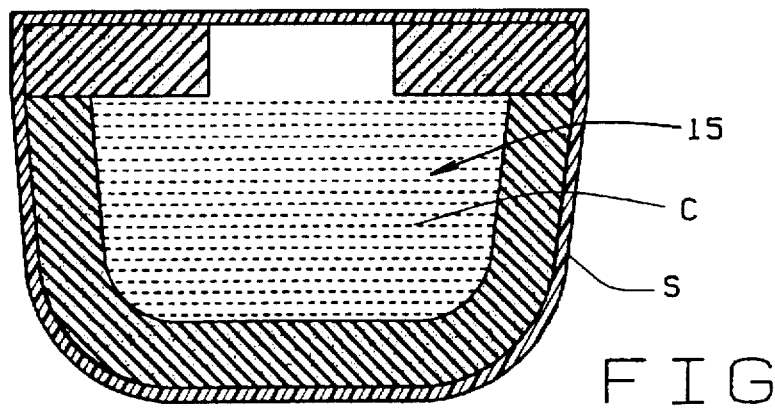
FIG. 9 is a cross-sectional view of the tray, pre-filled with a compound and which is sealed for transportation of the tray.

The tray assembly 1 can be provided either empty, as shown in the Figures, or with a selected compound C (such as fluoride) already in the channels 15, as shown in FIG. 9. If the trays are to be provided pre-filled with the compound, the trays will also be sealed to maintain the compound in place in the channel. The seal used can be any conventional seal which will close the gasket slot 19 to prevent the compound from escaping from the trays. For example, the trays can be totally covered or enclosed by a shrink warp S. Alternatively, a cover which extends over only the gasket to close the gap 19 can be used. Such a cover would be applied with a weak adhesive so that the cover could be easily removed from the tray.

Figure 10:
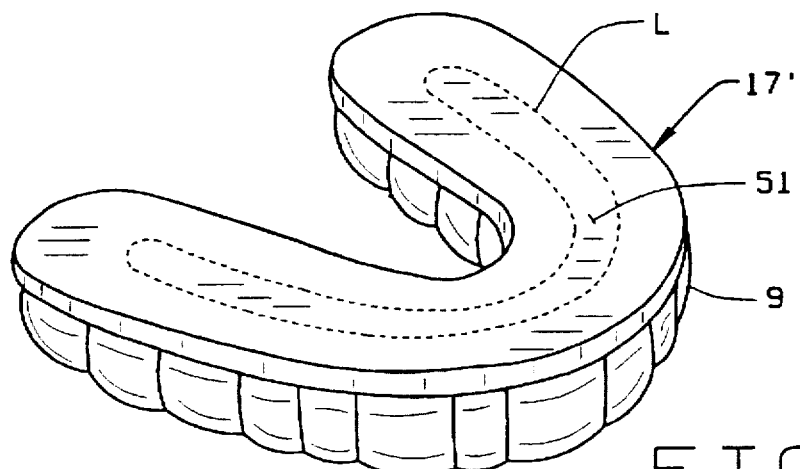
FIG. 10 is a perspective view of a tray with a covering which can be used to seal a prefilled tray for transportation, and which will form the gasket or flange of the tray.

In an other alternative, a cover 17' (FIG. 10) can be applied to the tray body 9 in lieu of the gasket 17. The cover 17' has a line of weakness L which will allow for the central material 51 of the cover 17' to be removed. The gap 19 would then be formed when this central strip 51 of material is removed from the cover 51. As can be appreciated, the cover 51 will also define the gasket which seals with the teeth and/or gums of the patient.

Figure 6:
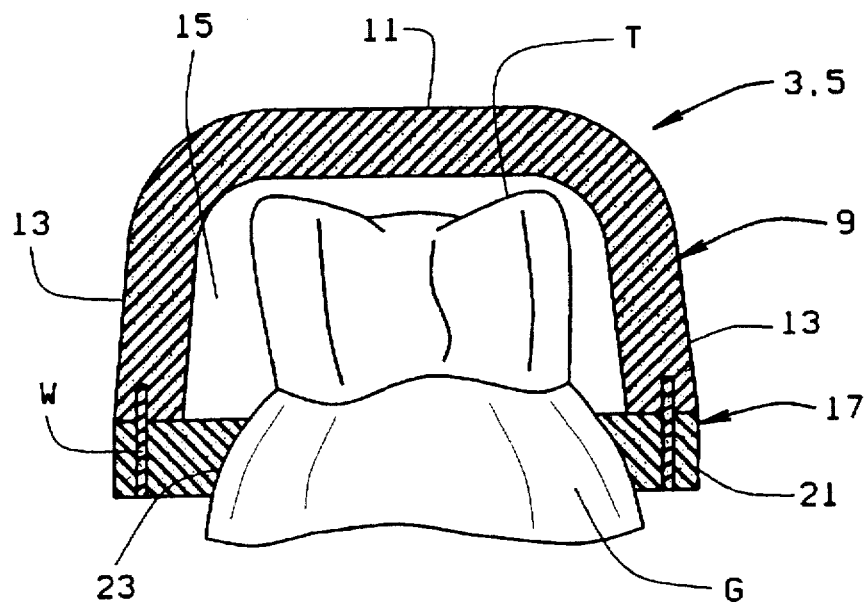
FIG. 6 is a cross-sectional view showing the tray assembly applied to a patient's teeth.

In use, the practitioner fills the channels 15 of the trays 3 and 5 with the compound, for example fluoride, to treat the teeth, if the tray is provided empty. If the tray is provided with the compound already in place, the tray assembly is opened for use. The tray assembly is then folded over, as shown in FIGS. 1 and 2 for insertion into a patient's mouth and application of the tray to the patient's teeth T. As noted, the handle/connector will extend through the patient's lips without distorting the patient's lips. When the trays are applied to the teeth, the inner edge 23 of the gasket 17 will seal against the patient's gums G and teeth, as seen in FIGS. 6-8. The closed cell foam of the body 9 will serve to hold the compound. The open cell foam of the gasket 17 will allow the gasket to conform to the irregularities of the patient's mouth, teeth, and gums to provide a substantially complete seal between the gums G and the tray body 9. Because the trays seal against the gums and the back of the rear molars, the gasket 17 substantially prevents the compound from leaking from the channel 15 into the patient's mouth. Further, the gasket 17, which is highly deformable, extends around the full circumference of the body 9, to provide a seal behind the last tooth. This seal behind the last tooth substantially prevents the compound from leaking out the rear of the tray and running down the patient's throat.

Figure 11:
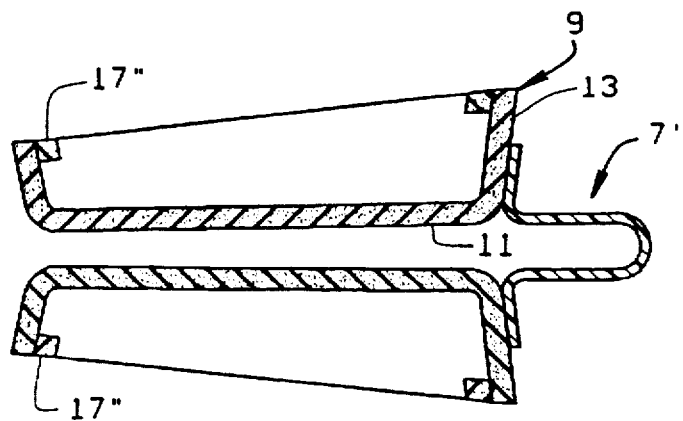
FIG. 11 is a cross-sectional view of the tray assembly showing an alternative manner of securing the connector or handle to the tray.

Turning to FIG. 11, an alternative connector 7' is shown. The connector 7' is substantially similar to the connector 7 of FIG. 1. However, rather than being fixed to the base of the tray body 9, an end portion of the connector is fixed to the outer surface of the wall 13 of the tray body 9. The tray of FIG. 11 is also shown with the gasket 17' fixed to the inner surface of the body wall 13, rather than along the edge of the body wall.

Figures 12, 13:
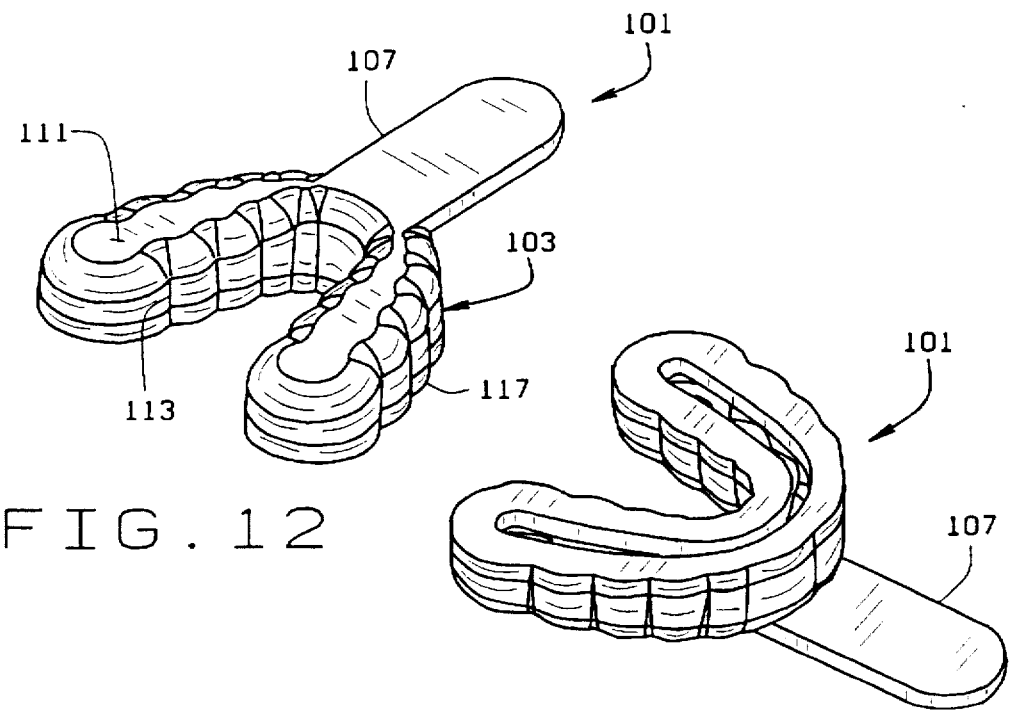
FIG. 12 is a bottom perspective view of a one-piece unitary dental tray including a handle.
FIG. 13 is a top perspective view of the one-piece tray.
Figures 14, 15, 16:
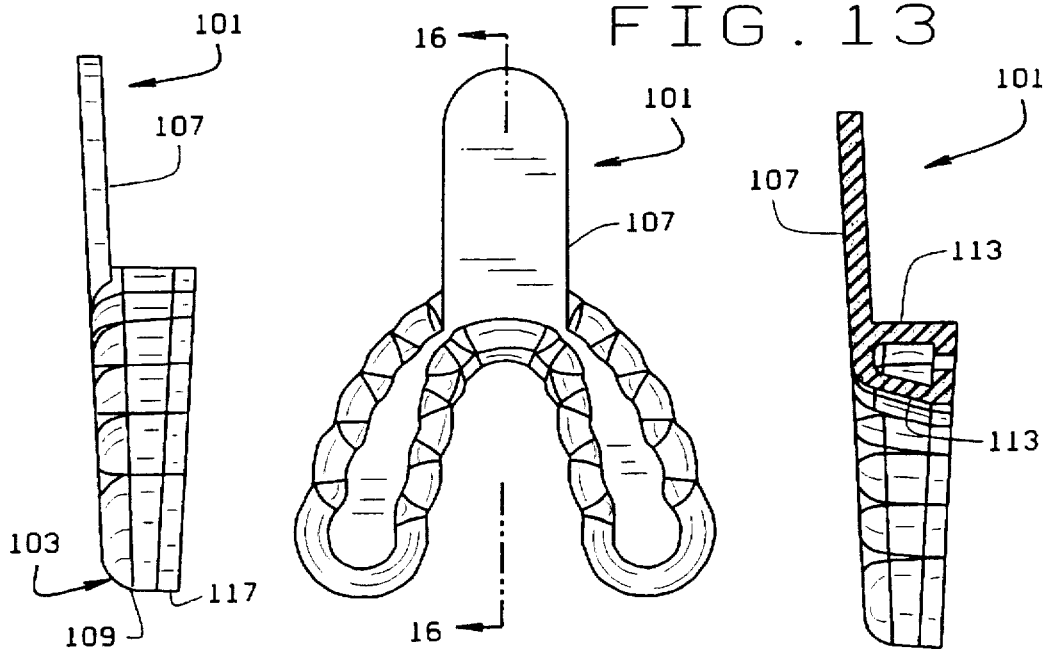
FIG. 14 is a side elevational view of the one-piece tray.
FIG. 15 is a bottom plan view of the one-piece tray.
FIG. 16 is a cross-sectional view of the one-piece tray taken along line 16—16 of FIG. 15.

FIGS. 12-16 show a further embodiment of the dental tray. The tray 101 is a one-piece tray wherein the tray 103, the handle 107, and the gasket 117 are molded together to form a one-piece unitary assembly. Because the tray 101 is a unitary tray, it is all made from one material, rather than from two, or three, different materials as is the tray assembly 1 of FIGS. 1-8. The tray 103 is substantially identical to the trays 3 and 5 of FIG. 1, and includes a tray body 109 and the gasket 117. However, as just noted, the gasket and tray body are molded as one-piece, rather than as two. The gasket portion 117 of the tray 103 is substantially identical to the gasket 17 of FIGS. 1-8. The body 109 includes a base 111 and a side wall 113. The handle 107, as best seen in FIGS. 12, 15, and 16, extends from the base 113 of the tray at the apex or center of the arch defined by the tray 103.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense. For example, although the invention was described with respect to a tray assembly, the trays could be separate from each other. Such individual trays could be provided with, or without, a handle. The tray body 9 can be made of other easily deformable, fluid-impervious materials which will hold the compounds used. Similarly, the gasket can be made from other flexible materials which will be easily deformed to conform to the contours of the patients gums and teeth. Although the gasket is shown to be fixed to the top surface of the tray wall, the gasket 17 could extend inwardly from the tray wall, such that the top surface of the gasket and the top edge of the wall are flush with each other. Although the tray 101 is shown as a single tray (i.e. an upper or lower tray), an upper and lower tray could be molded together as one piece, to form a one-piece unitary assembly which includes both the upper and lower trays joined by the connector which, when folded, forms the handle. These examples are merely illustrative.

We claim:

1. A dental tray for applying a compound to a patient's teeth, the tray comprising:

a body made from a generally fluid impervious material and having a base and side walls to define an arched channel sized and shaped to fit over a patient's teeth; and a flange extending inwardly from a top of the body wall, the flange defining a slot; said flange being sized and shaped to seal with the lingual and buccal surfaces of the patient's gums and/or teeth when the tray is applied to the patient's teeth.

2. The dental tray of claim 1 wherein said flange comprises a deformable gasket fixed to body wall.

3. The dental tray of claim 2 wherein said flange is fixed to the body along an upper edge of the body wall.

4. The dental tray of claim 2 wherein the tray body and flange are molded together as a one-piece unitary part.

5. The dental tray of claim 2 wherein the gasket is a foam gasket.

6. The dental tray of claim 1 wherein said slot has a width narrower than a width of the patient's teeth.

7. The dental tray of claim 6 wherein the slot varies in width from an apex of the tray to the back of the tray.

8. The dental tray of claim 7 wherein the slot has a width of about 0.05" at the apex of the tray to a width of between about 0.25" and 0.3" at the back of the tray.

9. The dental tray of claim 1 wherein the flange has a buccal portion and a lingual portion joined by a curved back portion.

10. The dental tray of claim 9 wherein the flange back portion has a width generally equal to or greater than the buccal and lingual portions of the flange.

11. The dental tray of claim 1 wherein the body is made from a flexible material.

12. The dental tray of claim 11 wherein the tray body is made from a foam.

13. The dental tray of claim 12 wherein the tray body is made from a closed-cell foam.

14. The dental tray of claim 1 wherein the tray is sized and shaped such that the flange is positioned above a gum line on the patient's upper jaw and below a gum line of the patient's lower jaw when applied to the patient's teeth.

15. The dental tray of claim 1 wherein the depth of said channel tapers from front to back, such that the back of the channel is shallower than the front of the channel.

16. The dental tray of claim 15 wherein the taper is from about 2° to about 17°.

17. The dental tray of claim 1 further including a handle; the handle extending from the base of the tray at the approximate apex of the tray.

18. The dental tray of claim 17 wherein the handle extends from a face of the tray at the approximate center of the tray, the handle having a preformed L-shape.

19. The dental tray of claim 17 wherein the handle and tray are molded together as a one-piece unitary part.

20. The dental tray of claim 1 wherein the tray channel is pre-filled with the compound to be applied to the teeth.

21. The dental tray of claim 1 wherein the tray is tray is individually wrapped in a sealed package.

22. A dental tray assembly for applying a compound or medicament to a patient's teeth; the tray assembly comprising:

an upper tray and a lower tray, said upper and lower trays each having a curved lingual wall, a buccal wall, and a base wall defining an arched channel adapted to fit over the patient's teeth;

a flange extending inwardly from the lingual and buccal walls of each tray, the flange defining slot in each tray sized to permit the patient's teeth to enter the channel;

a connector extending between said upper and lower trays and having opposed ends; said ends of said connector extending from the apex of the trays adjacent the base of the trays; said connector defining a handle when said trays are inserted into a patient's mouth, said handle being positioned to extend from a position generally between the patient's teeth and lips.

23. A dental tray assembly for applying a compound or medicament to a patient's teeth; the tray assembly comprising:

an upper tray and a lower tray, said upper and lower trays each comprising:

a body made from a generally fluid impervious lateral and having a curved lingual wall, a buccal wall, and a base wall defining an arched channel adapted to fit over the patient's teeths; and a deformable, arched gasket extending along an upper edge of the body lingual and buccal walls, the gasket extending inwardly from the body lingual and buccal walls; the gasket defining an arched slot positioned over said channel; said gasket forming a seal with the patient's gums and/or teeth when the tray is applied to the patient's teeth; and a connector extending between said upper and lower trays and having opposed ends; said ends of said connector extending from the apex of the trays adjacent the base of the trays; said connector defining a handle when said trays are inserted into a patient's mouth, said handle being positioned to extend from a position generally between the patient's teeth and lips.

24. The dental tray assembly of claim 23 wherein said connector has end edges.

25. The dental tray of claim 24 wherein the end edges of the connector correspond generally to the curvature of the lingual walls of the trays.

26. The dental tray assembly of claim 23 wherein said connector has a gripping surface defined by a pattern formed in the connector.

27. The dental tray assembly of claim 23 wherein said connector is a separate piece which is fixed to the upper and lower trays.

28. The dental tray assembly of claim 27 wherein the connector is fixed to the bases of the upper and lower trays.

29. The dental tray assembly of claim 23 wherein said gasket is sized and shaped to seal with the lingual and buccal surfaces of the patients gums, as well as with a back surface of the patients back teeth.

30. The dental tray assembly of claim 23 wherein the trays of the assembly are pre-filled with the compound to be applied to the teeth.

31. A dental tray assembly for applying a compound or medicament to a patient's teeth; the tray assembly comprising:

an upper tray and a lower tray, said upper and lower trays each having a curved lingual wall, a buccal wall, and a base wall defining an arched channel adapted to fit over the patient's teeth; and a connector extending between said upper and lower trays and having opposed ends; said ends of said connector extending from the apex of the trays adjacent the base of the trays; said connector defining a handle when said trays are inserted into a patient's mouth, said handle being positioned to extend from a position generally between the patient's teeth and lips the dental tray assembly being individually wrapped in a sealed package.

32. A dental tray for applying a compound to a patient's teeth, the tray comprising:

a body made from a generally fluid impervious material and having a bottom and side walls to define an arched channel sized and shaped to fit over a patient's teeth; and a flexible flange extending inwardly from a top of the tray wall, the flange defining slot sized to permit the patient's teeth to enter the channel;

said channel being pre-filled with the compound to be applied to the teeth; and a removable seal adapted to close the slot.

33. The dental tray of claim 32 wherein the seal comprises a shrink wrap covering, said shrink wrap covering being sized to cover at least the flange of the tray.

34. The dental tray of claim 32 wherein the seal comprises a cover adapted to close the slot.

35. The dental tray of claim 32 wherein the seal comprises a sheet which covers the channel, the sheet having a line of weakness corresponding to the shape of the slot; wherein the flange is formed when material within the line of weakness is removed from the sheet.

* * * * *